United States Patent [19]

Saito et al.

[11] Patent Number: 5,017,134

[45] Date of Patent: May 21, 1991

[54] DENTAL SYSTEM FOR TREATING A ROOT CANAL

[75] Inventors: Tsuyoshi Saito, 4-20-9-307, Kamisaginomiya, Nakano-ku, Tokyo; Masaru Yamaoka, Chiba, both of Japan

[73] Assignees: Tsuyoshi Saito; Masaru Yamaska; Masaichi Tanaka, all of Tokyo, Japan

[21] Appl. No.: 505,885

[22] Filed: Apr. 6, 1990

[30] Foreign Application Priority Data

Apr. 14, 1989 [JP] Japan .................................. 1-94478

[51] Int. Cl.$^5$ ............................................. A61C 19/04
[52] U.S. Cl. ...................................... 433/72; 433/224
[58] Field of Search .................... 433/72, 75, 224, 102

[56] References Cited

U.S. PATENT DOCUMENTS 3,660,901  5/1972  Inoue ..................................... 433/75
4,353,693  10/1982  Dery et al. ............................ 433/75

FOREIGN PATENT DOCUMENTS 0029689  11/1980  European Pat. Off. .
0205937  5/1986  European Pat. Off. .
62-2817  1/1987  Japan .

*Primary Examiner*—Cary E. Stone
*Assistant Examiner*—Andriene B. Lepiane
*Attorney, Agent, or Firm*—Fish & Richardson

[57] ABSTRACT

The present invention relates to dental equipment for treating a root canal. According to the present invention, two input signals with different frequencies are superposed. The difference between impedances corresponding to the two different frequencies at a given position in the root canal where the impedances hardly vary, is obtained. This value and a clinically determined value are used to detect the desired position in the root canal.

5 Claims, 5 Drawing Sheets

DENTAL SYSTEM FOR TREATING A ROOT CANAL

BACKGROUND OF THE INVENTION

1. Field of the Invention

The present invention relates generally to dental equipment for treating a root canal and in particular, to a system for automatically detecting any desired position in a root canal while enlarging the same. Such detection is possible even if the root canal is moisturized with liquid medicines.

2. Description of the Related Art

In endodontics, germs and the like are generally found in the root canal. Particularly, when the root canal is infected, germs and the like may enter deeply into the dentin. Both mechanical and chemical means are used to eliminate such germs in the root canal in an effort to prevent further infection. Also, the root canal should be fully closed all the way to its apical foramen so as to completely eliminate germs.

Accordingly, it is essential to accurately detect the position of the end of the root canal, known as the apical foremen, by mechanical means such as by a reamer or a file.

In order to measure the length of the root canal, three different methods have heretofore been used in combination: those methods comprise determining by hand when a file is in contact with the apical foramen, taking an X-ray with a reamer inserted in the root canal, or electrically detecting the apical foramen by means of impedance variations. A mechanical cutter such as a hand-operated reamer or file, or an engine reamer or ultrasonic cutter, is then used to enlarge the root canal. It is, however, difficult even for a skilled dentist to efficiently perform such a series of operations, which are time-consuming and may cause patients to suffer severe pain.

FIG. 5 shows a system designed to overcome the foregoing disadvantages. Specifically, this prior art system includes a mechanical cutter 2 having an electrode 3 in the form of a reamer to be inserted into a root canal 1. Another or counter electrode 5 is placed in contact with an oral membrane 4. The two electrodes 3, 5 are coupled to an electrical means 6 for detecting any given position in the root canal. The electrical means 6 is, in turn, coupled to a relay switch 7. The reamer 3 is used to enlarge the root canal 1 as it is advanced toward the apical foramen 8. The electrical means 6 functions to detect a change in impedance between the two electrodes 3, 5. This change may occur when the reamer 3 reaches the apical foramen 8. The relay switch 7 receives an output signal from the electrical means 6 whereby the mechanical cutter is stopped.

In this prior art system, the electrical measuring means 6 has an alternating power source with a frequency of 200 Hz. When the reamer 3 reaches the apical foramen 8, the value of a voltage is measured. This value is then used as a reference value indicating that the reamer has reached the apical foramen. It is reported, however, that such a value may vary depending on age of patients, type of teeth, or shape of the root canal involved. Thus, accurate measurement or detection can not be expected. Also, the interior of the root canal must be dried when the system is in use. During the enlargement of the root canal, the reamer may be bent or otherwise broken due to frictional contact with the dentin.

There has recently been developed a system for detecting any given position in the root canal by means of impedance differential. Voltages as used have different frequencies, for example, 1 KHz and 5 KHz. Waveforms of those frequencies are superposed to provide a composite or voltage waveform. Impedance of a tooth may vary depending on the two different frequencies. Then, the difference between impedances depending on each of two frequencies is measured at a position in the root canal where a change in impedance is low. When the difference becomes the smallest, it is understood that the reamer has reached the apical foramen. Accurate detection of any given position in the root can thus be effected regardless of the age of the patients, type of teeth or shape of the root canal involved.

Liquid medicines and the like which are used to clean the interior of the root canal are high in electrical conductivity or low in electrical resistivity. The difference suffers a dispersion in the vicinity of the apical foramen where the impedance of the tooth is low due to the presence of liquid medicines and the like. As a result, the prior art system cannot accurately detect the position of the apical foramen in the event that liquid medicines and the like are present in the root canal. Furthermore, the prior art system cannot be operative while the root canal is being enlarged.

SUMMARY OF THE INVENTION

Accordingly, it is an object of the present invention to provide an improved system for accurately detecting any given position in the root canal while enlarging the same. The present system can be operative, even if the root canal is moisturized with liquid medicines or blood.

In accordance with the present invention, two input signals having different frequencies are superposed. The difference between impedances corresponding to the two different frequencies at a given position in the root canal where the impedances may hardly vary, is obtained. This value and a clinically determined value are used to detect the desired position in the root canal.

Therefore, the system is capable of accurately detecting any position in the root canal, even the position of the apical foramen where impedances may vary widely due to the presence of liquid medicines or blood. The system is, therefore, fully operable under any conditions while enlarging the root canal.

BRIEF DESCRIPTION OF DRAWINGS

A better understanding of the present invention may be had by referring to the following detailed description of the preferred embodiments when taken in conjunction with the accompanying drawings, in which.

DETAILED DESCRIPTION OF THE PREFERRED EMBODIMENTS

Figure 1:
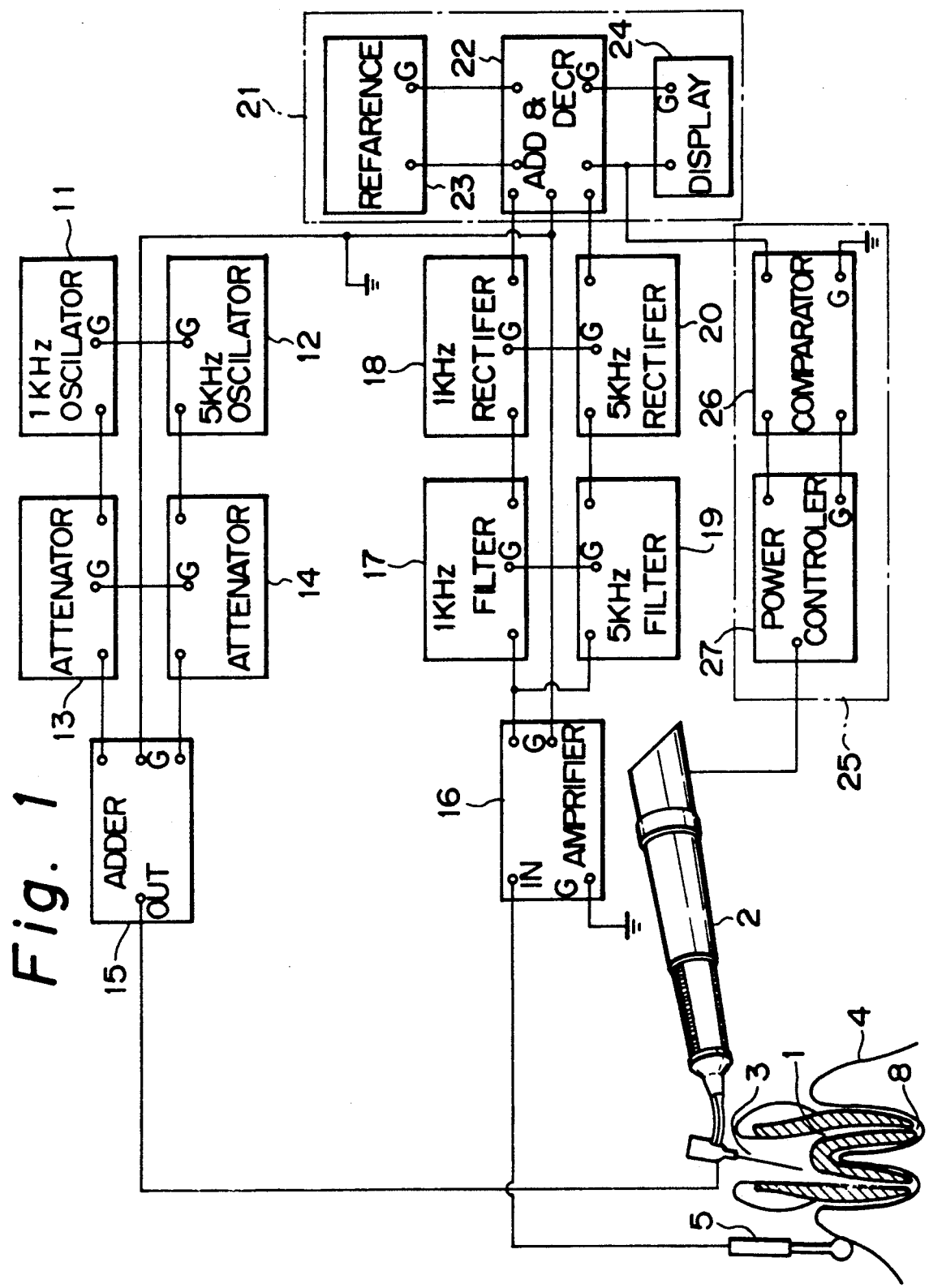
FIG. 1 is a block diagram showing the principal part of a circuit constructed according to one embodiment of the present invention.
Figure 5:
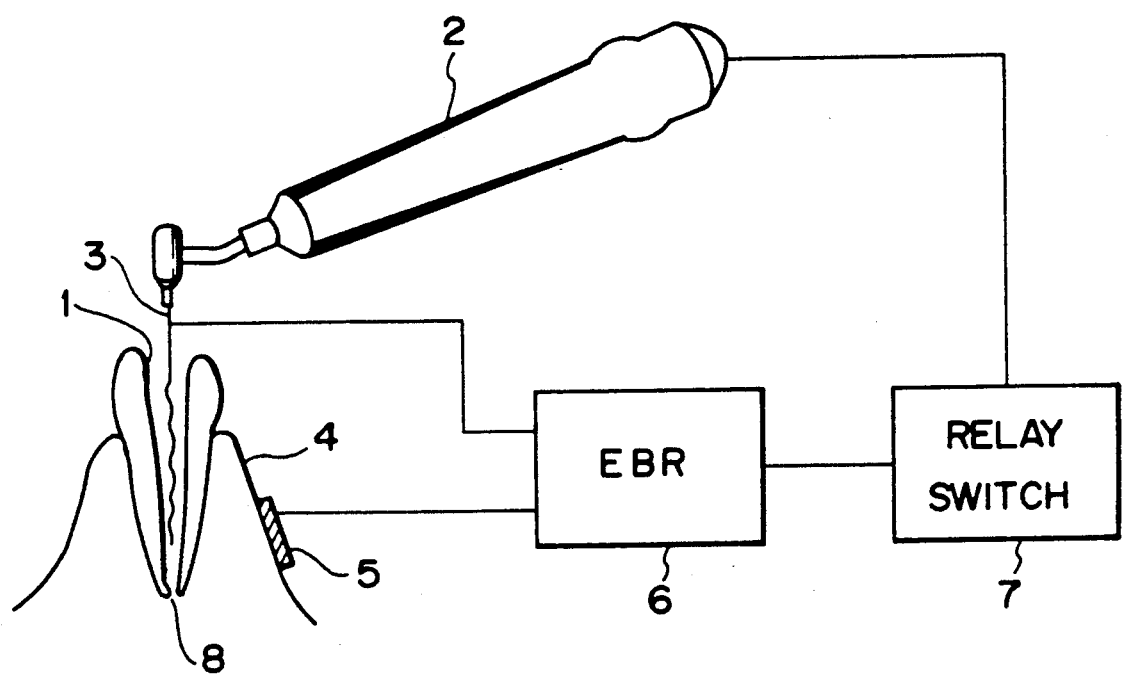
FIG. 5 is a view of a prior art system for explanation.

FIG. 1 is a block diagram showing the principal part of a system according to one embodiment of the present invention. Through FIGS. 1 and 5, like reference numerals are used to designate like or corresponding components.

In FIG. 1, the reference numerals 11, 12 designate oscillators for generating signals having frequencies of 1 KHz and 5 KHz. The oscillators 11, 12 are both coupled to attenuators 13, 14, respectively which are coupled to a common adder 15. The adder 15 is coupled to an electrode or reamer 3. Another or counter electrode 5 is coupled to an amplifier 16. This amplifier 16 is coupled, through a band-pass filter 17 and a rectifier 18 and through a band-pass filter 19 and a rectifier 20, to an adder-subtracter 22 in an "auto-reference" section 21 which is one of the main features of the present invention. The adder-subtracter 22 is coupled to a reference circuit 23 and a display 24.

The adder-subtracter 22 is also coupled to a comparator 26 in a cutter control section 25 which is another feature of the present invention. The comparator 26 is coupled to a power controller 27 which is, in turn, coupled to a mechanical cutter 2.

Figure 2:
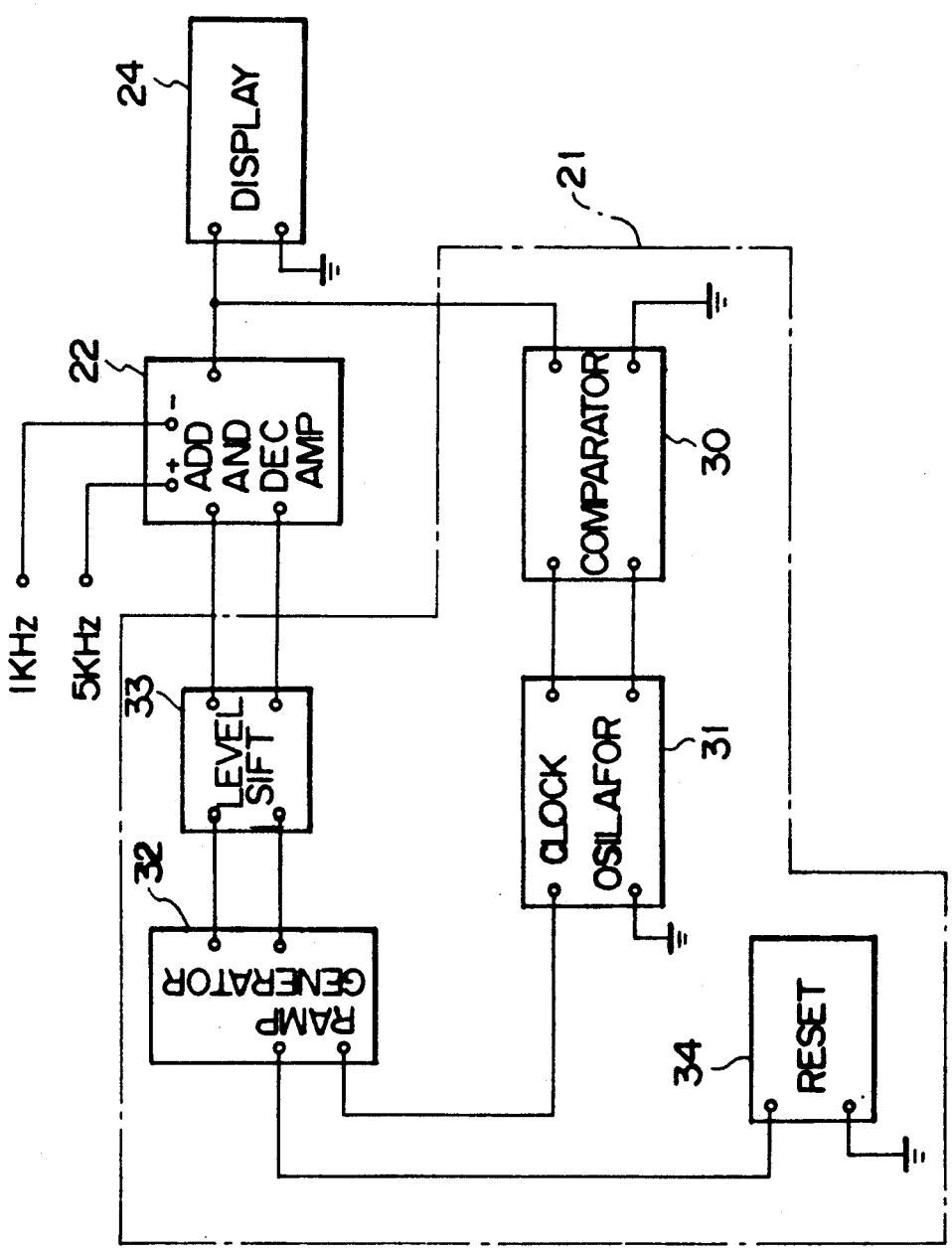
FIG. 2 is a detailed view of an auto-reference section.

The auto-reference section 21 is shown in detail in FIG. 2 wherein like reference numerals designate like or corresponding components in FIG. 1. As shown in FIG. 2, the rectifiers 18 and 20 are coupled to − terminal and + terminal in the adder-subtracter 22, respectively. The adder-subtracter 22 is also coupled to the display 24 as well as one of the terminals in the comparator 30. The comparator 30 is coupled to a clock generator 31 which is, in turn, coupled to a ramp generator 32. The ramp generator 32 is coupled to a level shifter 33 which is, in turn, coupled to another − terminal in the adder-subtracter 22. The reference numeral 34 designates a reset circuit coupled to the ramp generator 32.

OPERATION (a) Principle of Measurement

Figure 3:
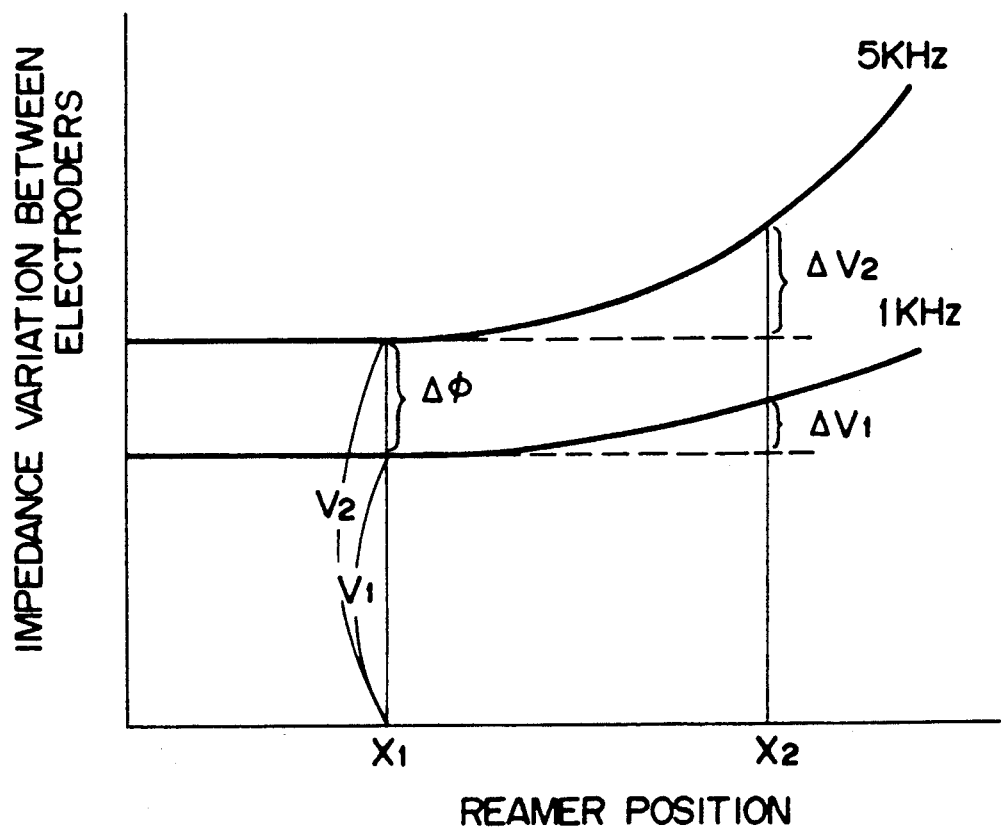
FIG. 3 is a graph showing change in impedance vs. position of a reamer.

FIG. 3 is a graph of experimental results showing a change in impedance between the reamer and the counter electrode in response to two different frequencies. The Y-axis indicates a change in impedance between the reamer 3 and the other electrode 5 in response to the frequencies of 1 KHz and 5 KHz, respectively. The X-axis indicates displacement or position of the reamer 3 within the root canal. It will be noted that the Y-axis is represented by voltage. This is because the voltage may vary in accordance with a change in the impedance.

As is well known, when the reamer 3 is located in the vicinity of a tooth neck or cervix of the tooth ($X_1$ in FIG. 3) where the impedance is high, the frequency responsive impedances are substantially kept constant. In contrast, when the reamer 3 is located in the vicinity of the apical foramen ($X_2$ in FIG. 3) where impedance is low, the frequency responsive impedances may be widely changed. As shown in FIG. 3, when the reamer 3 is located in the tooth neck $X_1$, the impedance hardly vary, and the voltages $V_1$ and $V_2$ are produced in response to the frequencies of 1 KHz and 5 KHz, respectively.

It should be noted, again, that the impedances between the reamer 3 and the other electrode 5 may vary widely when the reamer 3 is located in the vicinity of the apical foramen depending on the kinds of liquid medicines used or the presence of blood in the root canal. In the prior art system, however, actual differences between the impedances in response to the two frequencies was taken. Thus, accurate measurement or detection could not be effected when the reamer 3 is located in the vicinity of the apical foramen. To avoid this, in the present invention, a relative change in the impedance is considered for measurement purposes. Specifically, compensation (hereinafter referred to as reference compensation) is made, so that the difference between the voltages $V_1$ and $V_2$ becomes zero in the tooth neck $X_1$ where the impedances are substantially constant. In this way, liquid medicines and blood in the root canal will no longer affect the impedance variations.

$$\Delta\phi = V_2 - V_1 \quad (1)$$

The difference $\Delta\phi$ is now added to $V_1$ so as to compensate the value of a voltage for the frequency of 1 KHz at each position of the reamer. The difference Vf between the value of voltage $V_1$ thus compensated and the voltage $V_2$ when the reamer is positioned in the apical foramen is then represented as follows:

$$\begin{aligned} Vf &= (V_2 + \Delta V_2) - [(V_1 + \Delta\phi) + \Delta V_1] \\ &= (V_2 + \Delta V_2) - [(V_1 + V_2 - V_1) + \Delta V_1] \\ &= \Delta V_2 - \Delta V_1 \end{aligned} \quad (2)$$

According to the equation (2), $V_1$ and $V_2$ are no longer considered for taking the difference between the two impedances. Such a difference is now taken from a relative change in the impedances so as to eliminate any impedance variations due the presence of liquid medicines and the blood. As reference compensation is effected in the present invention, the compensated value allows accurate detection or measurement no matter whatever the conditions may be.

(b) Operation of the System

Operation of the system thus constructed will now be described. In the description, the position of the apical foramen is detected, it will be understood, however, that the system is capable of detecting any desired position in the root canal.

With reference to FIG. 1, the oscillators 11, 12 provide power voltages with frequencies of 1 KHz and 5 KHz, respectively. These voltages pass through the attenuators 13, 14. Waveforms of the two different frequencies are superposed to provide a composite waveform. The oscillators 13, 14 are so adjusted that the voltages with the respective frequencies of 1 KHz and 5 KHz are added in the ratio of 1 to 1 in the adder. The resultant waveform is a constant waveform having a maximum amplitude of 20 mVp-p. A voltage with such a resultant waveform is applied between the reamer 3 and the electrode 5. The voltages between the reamer 3 and the electrode 5 may vary depending upon impedance variations and are amplified by the amplifier 16. The voltages thus amplified pass through the band-pass filters 17, 19 so as to provide sinusoidal waveforms of 1 KHz and 5 KHz, respectively. These voltage waveforms are then rectified as a direct current through the rectifiers 18, 20. The rectified DC voltages corresponding to the voltages with the frequencies of 1 KHz and 5 KHz are applied to terminals at the subtracter and adder sides of the adder-subtracter 22, respectively. The adder-subtracter 22 then provides a signal indicative of the difference between the voltages, and the indicator 24 indicates such difference in the display.

Now, the dentist uses the mechanical cutter 2 to cut the root canal 1. When he visually determines that the reamer 3 has reached the root canal 1, a switch (not shown) is turned on so that the auto-reference section 21 is rendered operative.

Reference compensation, one of the features of the present invention, will be described hereafter with reference to FIGS. 2 and 3.

The adder-subtracter 22 provides a signal indicative of the difference $\Delta\phi$ between the impedance responsive voltages $V_1$ and $V_2$ in the tooth neck $X_1$. The comparator 30 receives this signal and thereafter provides a signal to the clock generator 31. The clock generator 31 then provides a clock signal whereby the ramp generator 32 is controlled to provide a ramp voltage. The ramp voltage is shifted by the level shifter 33. The resultant voltage is then applied to another − terminal of the adder-subtracter 22. The foregoing operation continues until the adder-subtracter 22 provides zero voltage, or the difference $\Delta\phi$ is added to the impedance responsive voltage $V_1$ having a frequency of 1 KHz. This reference compensation causes the adder-subtracter 22 to provide zero voltage. When the comparator 30 detects such a zero voltage, it provides a signal to that effect whereby the clock generator 31 is stopped. At this time, a ramp voltage (or voltage differential $\Delta\phi$) in the ramp generator 32 is maintained until the ramp generator 32 receives a reset signal from the reset circuit 34. According to the invention, the dentist operates the switch so as to effect the reference compensation.

After the reference compensation has been effected, a relative difference between the impedance responsive voltages with the frequencies of 1 KHz and 5 KHz is taken as shown in the equation (2). In other words, the adder-subtracter 22 provides a signal indicative of the difference $Vf(\Delta V_2 - \Delta V_1)$ between the impedances. This difference is successively compared to a predetermined value in the comparator 26.

It will be noted that this predetermined value is clinically determined by detecting a certain position (for example, the apical foramen) in the root canal through X-ray or the like and obtaining the difference between the two impedance responsive voltages at the position as detected. This value is then stored in the comparator 26 as a predetermined value.

When the reamer 3 reaches the apical foramen as a position to be detected, the comparator 26 (FIG. 1) provides a signal to that effect. In this way, the position of the apical foramen is automatically detected. When the power controller 27 receives such a signal, the cutter is automatically stopped.

Figure 4:
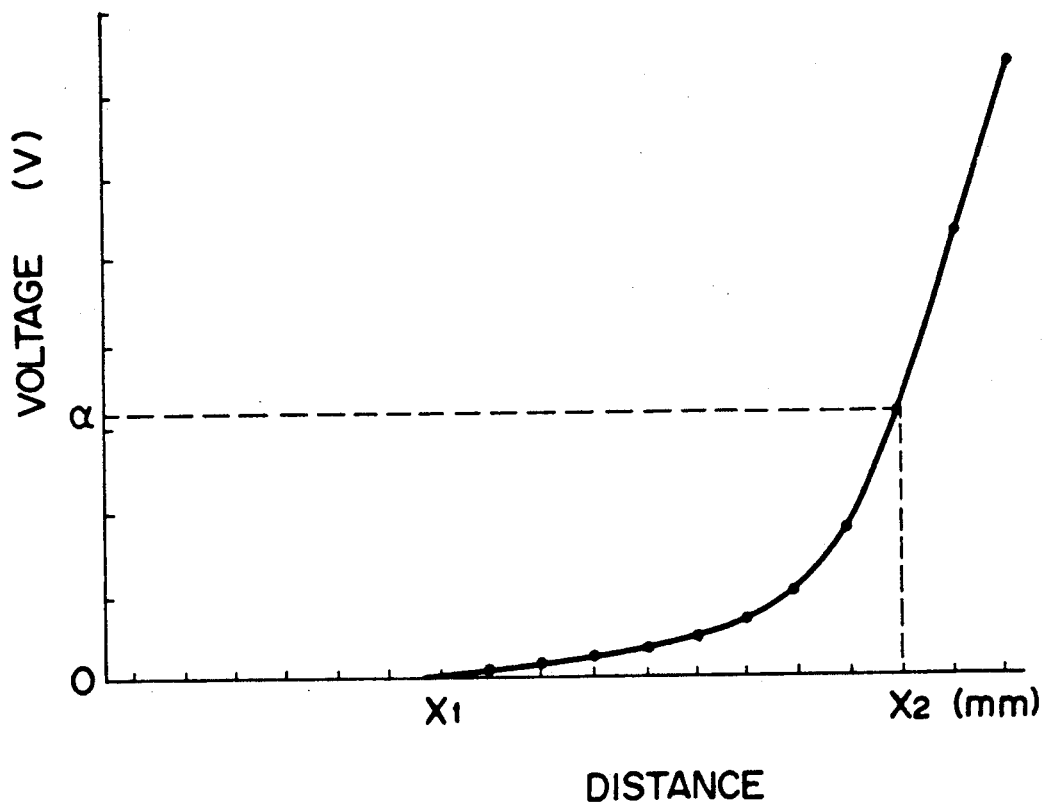
FIG. 4 is a graph showing an output waveform produced by an adder-subtracter after reference compensation has been effected.

FIG. 4 is a graph showing an output waveform provided by the adder-subtracter 22 after the reference compensation has been effected. In FIG. 4, Y-axis indicates voltage differential Vf, and X-axis indicates a position of the reamer, between the entry of the root canal and the apical foramen. As is clear from FIG. 4, the difference Vf is zero at the tooth neck $X_1$, and is substantially increased in the vicinity of the apical foramen. $\alpha$ in FIG. 4 indicates a predetermined value for detecting the position of the apical foramen.

As stated above, according to the present invention, two input signals having different frequencies are superposed. The difference between impedances corresponding to the two different frequencies at a given position in the root canal where the impedances may hardly vary, is obtained. This value and a clinically determined value are used to detect the desired position in the root canal.

Accordingly, the system is capable of accurately detecting any position in the root canal, even the position of the apical foramen where the impedances may widely vary in the presence of liquid medicines and bloods. Under any conditions, for example, when the root canal is moisturized, the system is fully operable while enlarging the root canal. The reamer is consequently hardly bent or broken.

Although various preferred embodiments of the invention have been described in detail, it will be appreciated that variations may be made without departing from the spirit of the invention or the scope of the appended claims.

What is claimed is:

1. A dental system for treating a root canal for detecting any given position in the root canal by means of impedance variations between a probe and a counter electrode corresponding to two different frequency signals, comprising:

first means for detecting respective impedance variations corresponding to said two different frequency signals;

second means for detecting a difference between the impedances at a given position in the root canal and determining a reference on the basis of said difference, said reference being used to detect the difference between the respective impedance variations; and third means for detecting a predetermined position in the root canal by said difference between the respective impedances obtained through said reference and a clinically determined value.

2. The system of claim 1, further including fourth means for controlling a cutter for enlarging and forming the root canal in response to a signal provided by said third means.

3. The system of claim 2, wherein said second means is so constructed as to add said difference between the respective impedances at said given position in the root canal to one of the impedance variations to thereby determine said reference.

4. The system of claim 1, wherein said second means is so constructed as to add said difference between the respective impedances at said given position in the root canal to one of the impedance variations to thereby determine said reference.

5. The system of claims 1, 2, 4 or 3, wherein said second means includes:

an adder-subtracter having a positive terminal and a negative terminal to which said respective impedance variations are respectively connected and providing an output indicative of a difference between said impedance variations;

a comparator determining whether said output provided by said adder-subtracter is zero; and a ramp generator providing a ramp voltage to said negative terminal of said adder-subtracter until said comparator provides a signal indicating that said output is zero and maintaining said ramp voltage when said comparator provides said signal.

* * * * *